US011032606B2

(12) United States Patent
Ashoori et al.

(10) Patent No.: US 11,032,606 B2
(45) Date of Patent: *Jun. 8, 2021

(54) SYSTEM, METHOD, AND RECORDING MEDIUM FOR PROVIDING NOTIFICATIONS IN VIDEO STREAMS TO CONTROL VIDEO PLAYBACK (71) Applicant: International Business Machines Corporation, Armonk, NY (US)

(72) Inventors: Maryam Ashoori, White Plains, NY (US); Elham Khabiri, Briarcliff Manor, NY (US); Justin David Weisz, Stamford, CT (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/270,756

(22) Filed: Feb. 8, 2019

(65) Prior Publication Data
US 2019/0174183 A1 Jun. 6, 2019

Related U.S. Application Data (63) Continuation of application No. 15/235,953, filed on Aug. 12, 2016, now Pat. No. 10,250,940.

(51) Int. Cl.
*H04N 5/445* (2011.01)
*H04N 21/44* (2011.01)
(Continued)

(52) U.S. Cl.
CPC ....... *H04N 21/44008* (2013.01); *G06Q 10/00* (2013.01); *G06Q 50/22* (2013.01);
(Continued)

(58) Field of Classification Search
CPC ........... H04N 21/23418; H04N 21/466; H04N 21/8358; H04N 21/2407; H04N 21/44008;
(Continued)

(56) References Cited

U.S. PATENT DOCUMENTS 6,675,384 B1 * 1/2004 Block .................. H04N 7/06
348/E5.096
8,539,529 B2 9/2013 Sloo
(Continued)

OTHER PUBLICATIONS

United States Notice of Allowance dated Nov. 20, 2018, in U.S. Appl. No. 15/235,953.
(Continued)

*Primary Examiner* — Jivka A Rabovianski
(74) *Attorney, Agent, or Firm* — Anthony Curro, Esq.; McGinn I.P. Law Group, PLLC (57) ABSTRACT A video stream control method, system, and a computer program product include analyzing a video stream to identify a section of the video stream where a condition will occur, delivering a notification that the condition will occur in the section of the video stream and modifying the video stream before the section of the video stream is played, and selecting a type of delivery of the section of the video stream based on a set of rules factoring the condition and user data at a time of the notification.

10 Claims, 5 Drawing Sheets (51) Int. Cl.
*H04N 21/25* (2011.01)
*H04N 21/466* (2011.01)
*H04N 21/234* (2011.01)
*H04N 21/845* (2011.01)
*G06Q 10/00* (2012.01)
*G06Q 50/22* (2018.01)
*H04N 21/4415* (2011.01)
*H04N 21/45* (2011.01)
*H04N 21/442* (2011.01)

(52) U.S. Cl.
CPC ..... *H04N 21/23418* (2013.01); *H04N 21/251* (2013.01); *H04N 21/466* (2013.01); *H04N 21/845* (2013.01); *H04N 21/4415* (2013.01); *H04N 21/44218* (2013.01); *H04N 21/4532* (2013.01)

(58) Field of Classification Search
CPC ............. H04N 21/251; H04N 21/4542; H04N 21/234; H04N 21/475
USPC ...... 725/19, 25, 34, 37, 35, 115, 116, 28, 44
See application file for complete search history.

(56) References Cited

U.S. PATENT DOCUMENTS

| | | | |
|---|---|---|---|
| 9,326,030 B2 | 4/2016 | Lewis et al. | |
| 9,607,656 B1* | 3/2017 | Serce | G11B 27/11 |
| 2003/0093790 A1 | 5/2003 | Logan et al. | |
| 2003/0131351 A1* | 7/2003 | Shapira | A61B 5/16 |
| | | | 725/24 |
| 2005/0223237 A1* | 10/2005 | Barletta | G06F 3/011 |
| | | | 713/186 |
| 2008/0046930 A1* | 2/2008 | Smith | H04N 7/163 |
| | | | 725/46 |
| 2010/0211966 A1 | 8/2010 | Zhang et al. | |
| 2012/0324493 A1 | 12/2012 | Holmdahl et al. | |
| 2013/0283162 A1 | 10/2013 | Aronsson et al. | |
| 2015/0181291 A1* | 6/2015 | Wheatley | H04N 21/4542 |
| | | | 725/10 |
| 2015/0237598 A1 | 8/2015 | Yoshitomi et al. | |
| 2016/0127766 A1 | 5/2016 | Luk et al. | |
| 2016/0142407 A1 | 5/2016 | Chun et al. | |
| 2016/0350609 A1 | 12/2016 | Mason et al. | |
| 2016/0381415 A1 | 12/2016 | Vijay et al. | |
| 2017/0178692 A1* | 6/2017 | Wouhaybi | H04N 21/437 |

OTHER PUBLICATIONS

United States Office Action dated Sep. 7, 2018, in U.S. Appl. No. 15/235,953.
United States Office Action dated Jun. 11, 2018, in U.S. Appl. No. 15/235,953.
United States Office Action dated Mar. 7, 2018, in U.S. Appl. No. 15/235,953.
United States Office Action dated Dec. 12, 2017, in U.S. Appl. No. 15/235,953.
United States Office Action dated Sep. 20, 2017, in U.S. Appl. No. 15/235,953.
United States Office Action dated Aug. 14, 2017, in U.S. Appl. No. 15/235,953.
Mel, et al. "The NIST Definition of Cloud Computing". Recommendations of the National Institute of Standards and Technology. Nov. 16, 2015.
IBM (2009). "Method for DVR to Detect and Notify User of Ability to Skip the Viewing of Advertisement". IBM TDB. ip.com000179149D. Feb. 7, 2009.

* cited by examiner

SYSTEM, METHOD, AND RECORDING MEDIUM FOR PROVIDING NOTIFICATIONS IN VIDEO STREAMS TO CONTROL VIDEO PLAYBACK

CROSS-REFERENCE TO RELATED APPLICATIONS

The present application is a Continuation Application of U.S. patent application Ser. No. 15/235,953, filed on Aug. 12, 2016, the entire contents of which are hereby incorporated by reference.

BACKGROUND

The present invention relates generally to a video stream control system, and more particularly, but not by way of limitation, to a system for providing a notification in a video stream that a section of the video stream will cause a condition to occur based on biometrics or user preferences and a selection of a type of delivery of the section of the video based on a set of rules and/or user input.

Conventional video stream control techniques consider tagging inappropriate content such as obscene or violent situations for a user. In some prior art techniques of filtering objectionable television programming, offensive language is detected, the audio is muted, and the closed-captioned broadcast signal is modified. The process may include monitoring the closed-captioned signal. Each captioned word is checked against a dictionary of offensive words stored. If an offensive word is detected, the audio is muted for the sentence, and the offensive word is removed from the closed-captioned signal. A suitable word is substituted for the profanity, when appropriate, and the replacement sentence is displayed on the screen in text form.

Other conventional techniques consider altering the content of the tagged scene by blurring the audio of the tagged scene, blurring the video of the tagged scene, and replacing undesired words with desired words in the tagged scene.

Thus, the needs in the art include a video control that does not drastically distort the content such that the user is unable to enjoy the content or at the very least, the user's mood is affected based on the distraction of distorting the content and a video control the content based on the content itself without considering a condition of the user.

SUMMARY

In an exemplary embodiment, the present invention can provide a video stream control method, including analyzing a video stream to identify a section of the video stream where a condition will occur, delivering a notification that the condition will occur in the section of the video stream and modifying the video stream before the section of the video stream is played, and selecting a type of delivery of the section of the video stream based on a set of rules factoring the condition and user data at a time of the notification.

One or more other exemplary embodiments include a computer program product and a system.

Other details and embodiments of the invention will be described below, so that the present contribution to the art can be better appreciated. Nonetheless, the invention is not limited in its application to such details, phraseology, terminology, illustrations and/or arrangements set forth in the description or shown in the drawings. Rather, the invention is capable of embodiments in addition to those described and of being practiced and carried out in various ways and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

Aspects of the invention will be better understood from the following detailed description of the exemplary embodiments of the invention with reference to the drawings, in which.

DETAILED DESCRIPTION OF THE EXEMPLARY EMBODIMENTS

The invention will now be described with reference to FIG. 1-5, in which like reference numerals refer to like parts throughout. It is emphasized that, according to common practice, the various features of the drawing are not necessarily to scale. On the contrary, the dimensions of the various features can be arbitrarily expanded or reduced for clarity.

Figure 1:
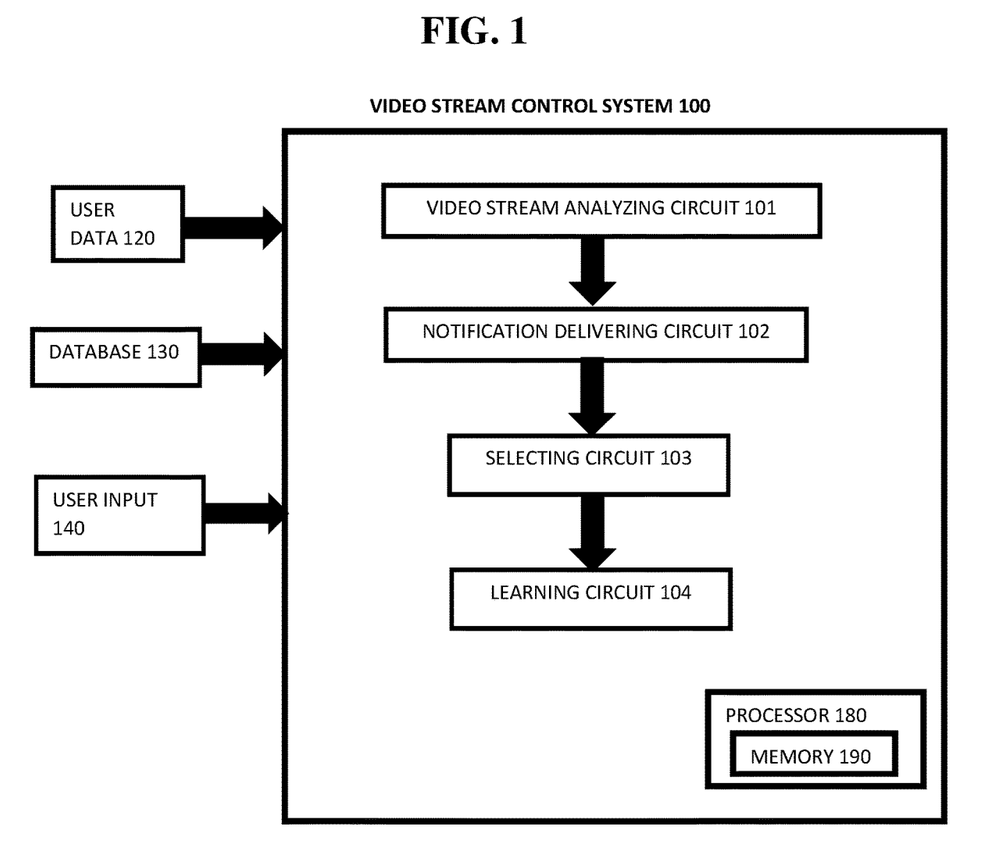
FIG. 1 depicts a block diagram illustrating a video stream control system according to an embodiment of the present invention.

With reference now to the example depicted in FIG. 1, the video stream control system 100 includes a video stream analyzing circuit 101, a notification delivering circuit 102, a selecting circuit 103, and a learning circuit 104. The video stream control system 100 includes a processor 180 and a memory 190, with the memory 190 storing instructions to cause the processor 180 to execute each circuit of the video stream control system 100. The processor and memory may be physical hardware components, or a combination of hardware and software components.

Although the video stream control system 100 includes various circuits, it should be noted that a video stream control system can include modules in which the memory 190 stores instructions to cause the processor 180 to execute each module of the video stream control system 100.

Also, each circuit can be a stand-alone device, unit, module, etc. that can be interconnected to cooperatively produce a transformation to a result.

Thus, the video stream control system 100 according to an embodiment of the present invention may act in a more sophisticated, useful and cognitive manner, giving the impression of cognitive mental abilities and processes related to knowledge, attention, memory, judgment and evaluation, reasoning, and advanced computation. A system can be said to be "cognitive" if it possesses macro-scale properties—perception, goal-oriented behavior, learning/memory and action—that characterize systems (i.e., humans) generally recognized as cognitive.

Although one or more embodiments (see e.g., FIGS. 3-5) may be implemented in a cloud environment 50 (see e.g., FIG. 4), it is nonetheless understood that the present invention can be implemented outside of the cloud environment.

A section of a video stream where a condition will occur can be identified by the video stream analyzing circuit 101. That is, the video stream analyzing circuit 101 analyzes the video stream to determine a section (e.g., a scene of the video) that may cause a certain condition of the user to occur such as sudden stress, increased excitement level, potential heart attack-causing effects, parental supervision (e.g., section inappropriate for younger viewers) based on biometric data and/or user data 120 including user preferences. In other words, the video stream analyzing circuit 101 identifies scenes of a video stream that can cause a detrimental effect to the user, for example, by monitoring the biometrics of the user to determine if the scene will cause an increase in biometric data such as pulse, heart rate, stress, etc. The video stream can comprise a movie, television show, video game, virtual environment, video segment, still images presented in a stream, etc.

The determination can include a likelihood that the identified section of the video will have a negative effect on the user such as increase the user's heart rate, stress levels, etc. or include inappropriate content, such as age-restricted content. The condition can be based on health risks as determined by biometric data indicating that the health risk is increased based on watching the section of the video.

A list of relations between the user data 120 and/or biometric data and related condition(s) occurring can be included in database 130 and updated over time via learning as described later. In some embodiments, the user can configure or update user data 120 with biometric data threshold levels to indicate a condition may occur, such as setting a heart rate level that a section of the video causes to be exceeded in order to trigger the notification as described later. In another example, user data 120 can specify age restrictions for certain types of content (e.g., certain vulgar terms having different age limits or types of violence, etc.).

The notification delivering circuit 102 can modify (e.g., freeze, interrupt, stop, pause, etc.) the video stream and deliver a notification that the condition will occur in the section of the video stream before the section of the video stream is played. By way of example only, the notification delivering circuit 102 can be configured to notify a user that a section of the video has been identified as potentially causing a condition to occur that may be detrimental to the user and modifies (e.g., freezes) the video to display the notification prior to the potentially detrimental section being played, such that one or more actions can be taken (an example of which will described later).

In some embodiments, the timing of the notification being delivered can vary based on a user preference included in the database 130.

In some embodiments, the notification can comprise an audio emitted such as a buzzer noise, a caption including text describing the upcoming scene to the user, etc.

In some embodiments, the selecting circuit 103 selects a type of delivery of the section of the video stream based on a set of rules factoring (or correlating) the condition and user data at a time of the notification. That is, based on the notification being triggered by the condition being identified to occur, the selecting circuit 103 selects how to deliver (e.g., present) the section of the video stream in order to minimize the potential risks of the video stream to the user. For example, a type of delivery can include presenting only the audio of the section, skipping the section of the video, a textual summary, etc. In other words, the selecting circuit modifies the type of playback of the video stream based on a set of rules stored in the database 130 weighing the biometrics of the user or user data 120 with the condition identified to select the type of delivery that will be the least likely to cause the condition to occur.

For example, if the condition of concern is a heart attack and the biometric data of the corresponding user is within a range as defined by the set of rules that the scene may cause the condition to occur (e.g., the heart attack), the selecting circuit 103 can select a type of delivery that will lower the state of the biometric data of the user to avoid the possible heart attack.

The selecting circuit 103 can further query the user for a user input 140 to select the type of delivery based on the user's preference.

In some embodiments, the learning circuit 104 may learn, based on past reactions (e.g., from crowd sourcing information from multiple users) to the video stream, to improve identification of a potential condition by the video stream analyzing circuit 101. In some embodiments, sections of the video stream where the user data is greater than a predetermined threshold that did not cause a notification is learned for the notification delivering circuit to improve deliver a notification. In other words, the learning circuit 104 can learn if a condition was not properly identified and update the thresholds of the database 130 that trigger the condition to be identified.

In some embodiments, the learning circuit 104 can learn based on one or more user reactions to the type of delivery of the video stream selected by the selected circuit 103 to change the selected type of delivery, e.g., based on user reactions indicating an increased risk to the user. For example, set of rules of the database 130 might include a rule to the effect that if a user's heart rate is within ten percent of a threshold heart rate that can trigger a heart attack, the selecting circuit 103 could select an option of modifying a multimedia stream to play only the audio portion of the section of the stream of concern. In this case however, the learning circuit 103 has learned (based on user reactions) that the foregoing was not the best possible of available choices and updates the rule to cause the identified section of the multimedia stream to be skipped entirely when the biometric data of the user indicates that the heart rate is within ten percent of a heart attack condition.

In some embodiments, the learning circuit 104 can learn and adjust configurations based on one or more user reactions to multimedia streams. For example, if the selecting circuit 103 skips the graphic scenes or scenes of accidents, the learning circuit 104 can learn to provide warnings before such a scene. Or, if watching a certain scene causes a sudden pulse change, the learning circuit 104 can learn to provide warnings ahead of the time.

In some embodiments, the learning circuit 104 can learn by comparing similar profiles of users (e.g., users with similar condition to biometric data relationships) and can create emotional profiles for individuals and cluster them for further alerts. For example, the learning circuit 104 can learn where sections of media trigger increase in heart rate and other biometrics by aggregating data across previous viewers of the content.

Figure 2:
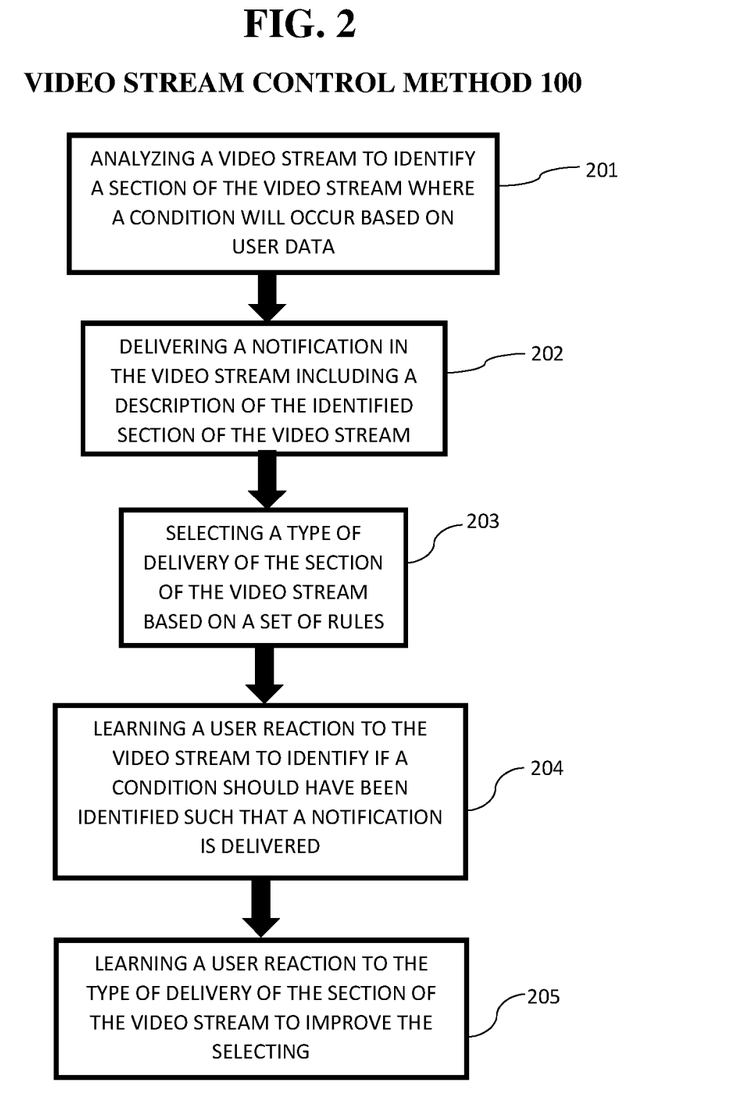
FIG. 2 depicts a flow chart for a video stream control method according to an embodiment of the present invention.

With reference now to the example depicted in FIG. 2, the video stream control method 200 includes various steps to provide notifications in a video stream to a user when a condition will occur based on biometrics and/or user preferences to change a form of the delivery of the video stream depending on the condition and the user. As shown in at least FIG. 3, one or more computers of a computer system 12 according to an embodiment of the present invention can include a memory 28 having instructions stored in a storage system to perform the steps of FIG. 2.

In step 201, a video stream can be analyzed to identify a section of the video stream where a condition will occur.

In step 202, a notification that the condition will occur in the section of the video stream can be delivered and the video stream can be modified before the section of the video stream is played.

In step 203, a type of delivery (presentation) of the section of the video stream can be selected based on a set of rules factoring the condition and user data at a time of the notification.

In step 204, a plurality of user reactions to the video stream can be learned to optimize the identification of the condition by the analyzing such that sections of the video stream where the user data is greater than a predetermined threshold that did not cause a notification is learned for the notification delivering to optimally deliver a notification.

In step 205, a plurality of user reactions to the type of delivery of the video stream selected can be learned to change the selected type of delivery based on the plurality of user reactions indicating an increase risk to the user.

It is noted that the user can provide a specific user input or user preference to state which types or scenes that the user wishes to avoid or which to be notified of before presenting.

Thus, the learning can be by crowd sourcing and/or reactions (and inputs/preferences) of the specific user.

In one exemplary embodiment, a user is a cardiac patient. She is discharged from the hospital and has been warned by her doctor to stay away from any situation that may cause a sudden excitement or heart pressure. The user is watching an action movie. The video stream analyzing circuit 101 identifies that the main character is about to get into an accident and die which could cause the user to have a heart attack (e.g., condition to occur). The notification delivering circuit 102 delivers a notification on her television that in fifteen seconds, an accident is about to happen. The movie has audio description available. The notification delivering circuit 102 automatically freezes the scene and the selecting circuit 103 plays the audio description of the scene instead (e.g., selects a type of delivery). When the accident scene is over, the video stream goes back to the normal mode. The selecting circuit 103 could also display a plurality of options for the user to select from for the type of deliver such as to watch the scene, to fast forward, receive a text summary of the scene as a caption, and listen to the audio description of the scene instead (the similar way as a blind watching the movie).

In another embodiment, parents and their nine-year old son are watching a movie. The notification delivering circuit 102 delivers a warning that in 30 second, an adult scene is about to be played. The selecting circuit 103 automatically selects to skip the scene based on a set of rules stating that if an adult scene is identified and a viewer is less than thirteen-years old, the scene should be skipped.

In another embodiment, the user can be playing video games and his heart rate has been going up. The system detects the user's high pulse from his smartwatch (e.g., a wearable). The user is about to walk into a hall full of attackers in the video game. The notification delivering circuit 102 delivers a warning that his pulse rate is irregularly high and he is about to experience sudden excitement while the selecting circuit 103 queries the user for a type of deliver of the content. The user can choose to pause the game, and take a rest, or skip that stage of the game.

Thus, the invention includes features that address one of the technical needs in the art by providing notifications (via a multimedia or video stream) to a user when a condition may or will occur, based on biometrics and/or user preferences, to change a form of the delivery of the stream content depending on the condition and the user.

Exemplary Aspects, Using a Cloud Computing Environment

Although this detailed description includes an exemplary embodiment of the present invention in a cloud computing environment, it is to be understood that implementation of the teachings recited herein are not limited to such a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client circuits through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 3:
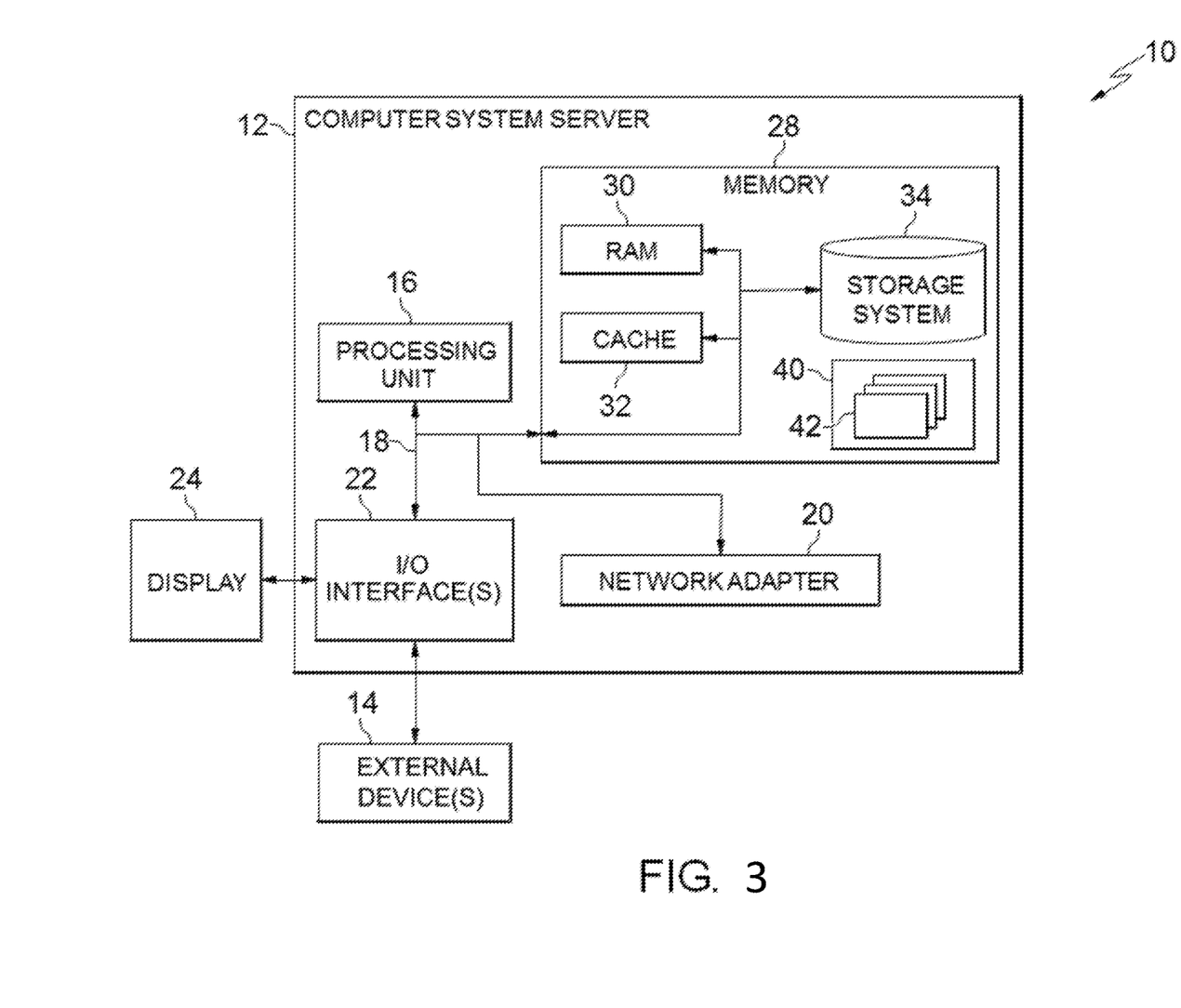
FIG. 3 depicts a cloud computing node according to an embodiment of the present invention.

Referring now to FIG. 3, a schematic of an example of a cloud computing node is shown. Cloud computing node 10 is only one example of a suitable node and is not intended to suggest any limitation as to the scope of use or functionality of embodiments of the invention described herein. Regardless, cloud computing node 10 is capable of being implemented and/or performing any of the functionality set forth herein.

Although cloud computing node 10 is depicted as a computer system/server 12, it is understood to be operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop circuits, multiprocessor systems, microprocessor-based systems, set top boxes, programmable consumer electronics, network PCs, minicomputer systems, mainframe computer systems, and distributed cloud computing environments that include any of the above systems or circuits, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing circuits that are linked through a communications network. In a distributed cloud computing environment, program modules may be located in both local and remote computer system storage media including memory storage circuits.

Referring again to FIG. 3, computer system/server 12 is shown in the form of a general-purpose computing circuit. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out various functions and/or methodologies of embodiments of the invention.

Computer system/server 12 may also communicate with one or more external circuits 14 such as a keyboard, a pointing circuit, a display 24, etc.; one or more circuits that enable a user to interact with computer system/server 12; and/or any circuits (e.g., network card, modem, etc.) that enable computer system/server 12 to communicate with one or more other computing circuits. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, circuit drivers, redundant processing units, external disk drive arrays, RAID systems, tape drives, and data archival storage systems, etc.

Figure 4:
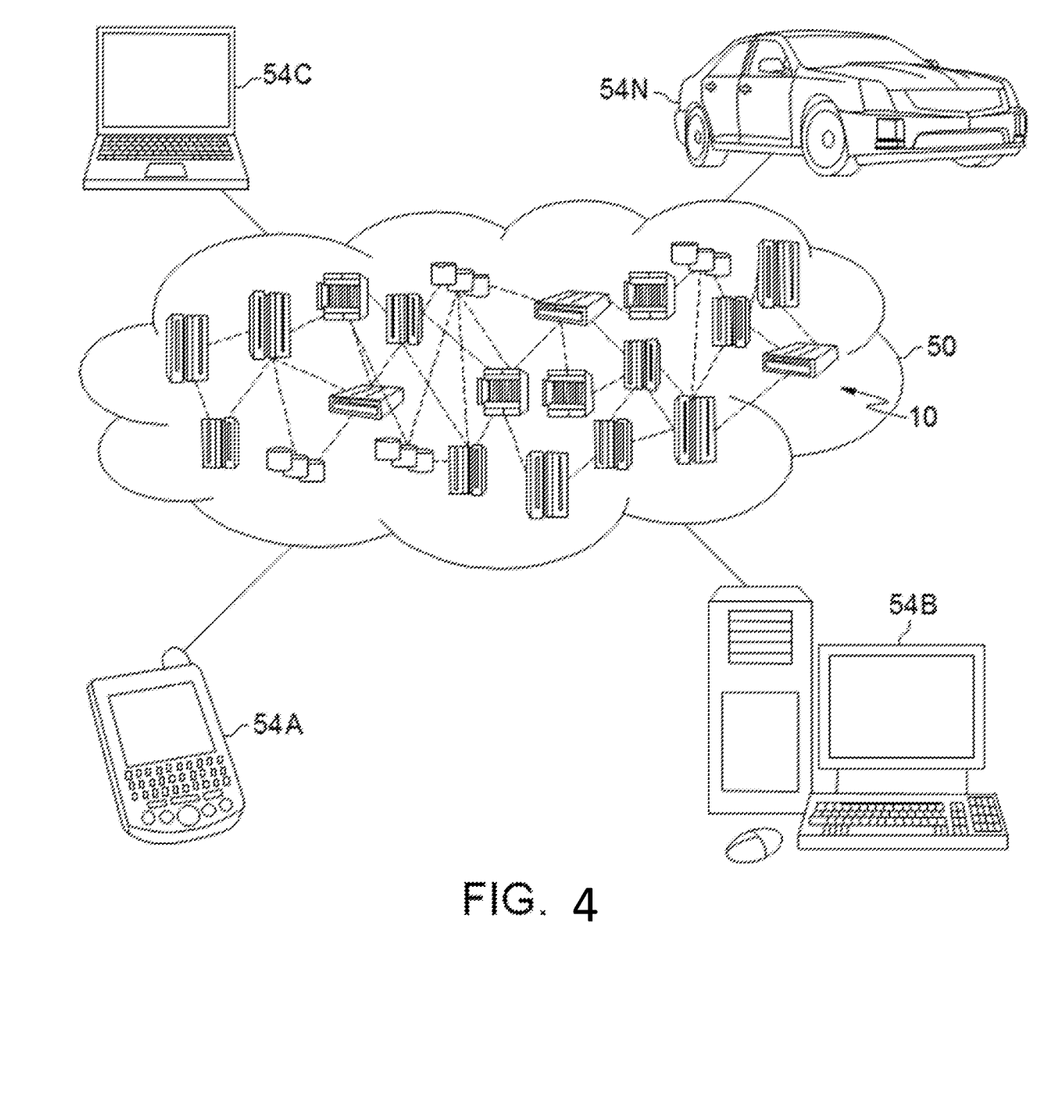
FIG. 4 depicts a cloud computing environment according to an embodiment of the present invention.

Referring now to FIG. 4, illustrative cloud computing environment 50 is depicted. As shown, cloud computing environment 50 comprises one or more cloud computing nodes 10 with which local computing circuits used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing circuit. It is understood that the types of computing circuits 54A-N shown in FIG. 4 are intended to be illustrative only and that computing nodes 10 and cloud computing environment 50 can communicate with any type of computerized circuit over any type of network and/or network addressable connection (e.g., using a web browser).

Figure 5:
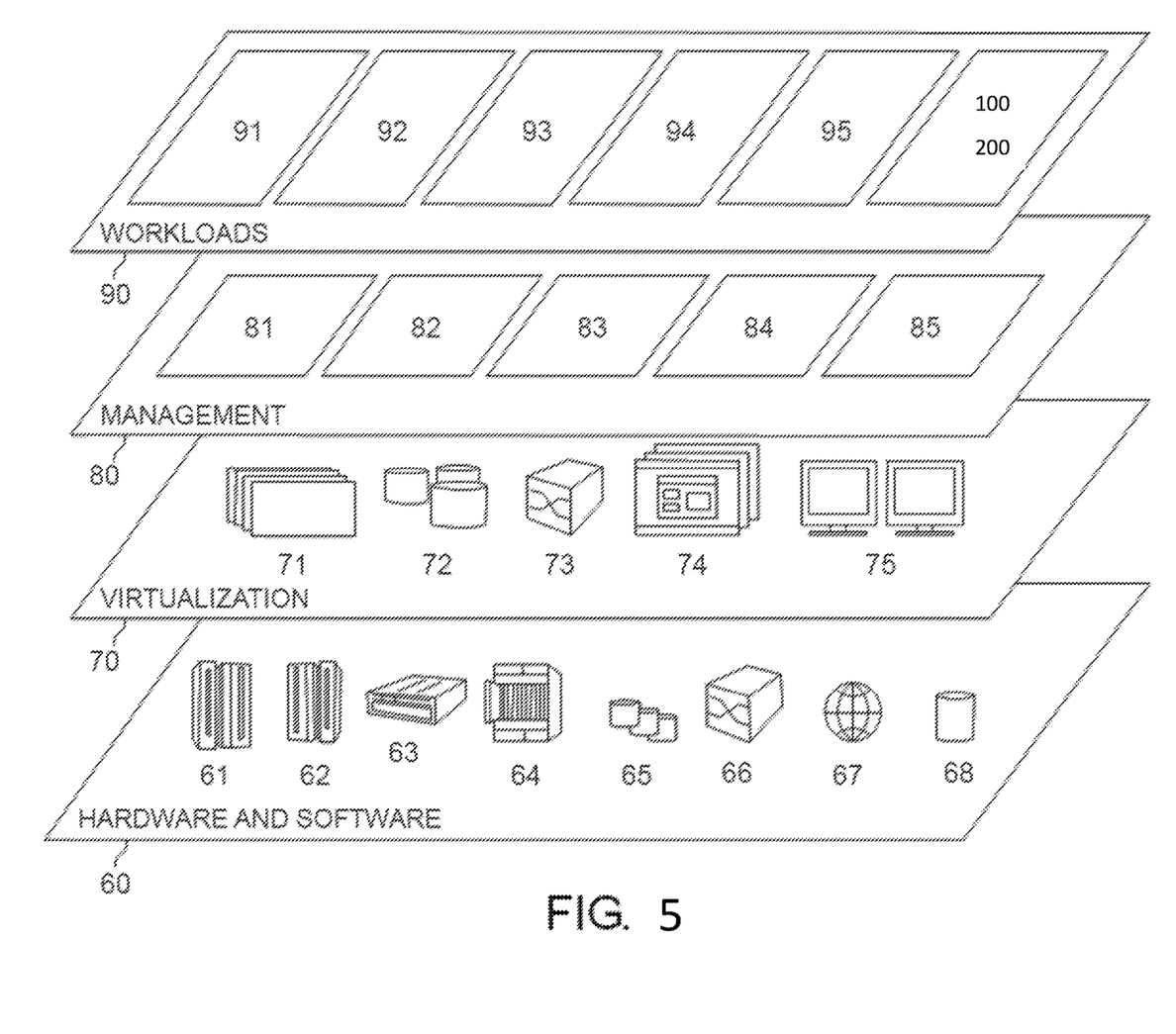
FIG. 5 depicts abstraction model layers according to an embodiment of the present invention.

Referring now to FIG. 5, an exemplary set of functional abstraction layers provided by cloud computing environment 50 (FIG. 4) is shown. The components, layers, and functions shown in FIG. 5 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage circuits 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and, more particularly relative to the present invention, the video stream control system 100 and method 200.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Further, Applicant's intent is to encompass the equivalents of all claim elements, and no amendment to any claim of the present application should be construed as a disclaimer of any interest in or right to an equivalent of any element or feature of the amended claim.

What is claimed is:

1. A video stream control system, the system comprising:
a video stream analyzing circuit configured to identify, apriori, a section of a video stream where an adverse condition will occur by determining, apriori, that a likelihood of the section of the video will have a negative effect is greater than a first predetermined threshold;
a notification delivering circuit configured to modify the video stream and to deliver a notification that the adverse condition will occur in the section of the video stream before the section of the video stream is played; and
a selecting circuit configured to select a type of delivery of the section of the video stream that includes a modified version of the section omitting the adverse condition based on a set of rules factoring the adverse condition and user data at a time of the notification,
wherein the selecting circuit, after the notification is delivered, queries for authorization to watch the unmodified version of the section of the video stream,
wherein a timing of the notification varies based on a user input, and
wherein a sensitivity of the video stream analyzing circuit identifying the adverse condition varies based on a user constraint to a predetermined threshold of biometric data required to trigger the adverse condition,
further comprising a learning circuit configured to learn a plurality of user reactions to the video stream to optimize an identification of the adverse condition by the video stream analyzing circuit.

2. The system of claim 1, wherein the user data comprises biometric data such that the set of rules causes the user data to select a type of delivery based on avoiding a health risk caused by viewing the video stream comprising the adverse condition as determined by the biometric data,
　　wherein the biometric data includes data determined based on an interval of time, and
　　wherein the first predetermined threshold is configurable by a user.

3. The system of claim 1, wherein the user data comprises a user preference such that the set of rules causes the selecting circuit to select a type of delivery customized to the user preference.

4. The system of claim 1, wherein the selecting circuit further queries to select the type of delivery based on a textual description of the section of the video stream, and
　　wherein the selecting circuit selects the type of delivery with consideration of a resultant mood based on the type of delivery selected.

5. The system of claim 1, wherein the notification delivering circuit interrupts the video stream by freezing the video stream when the section of the video stream comprising the adverse condition indicating a potential risk from viewing the section of the video stream is about to be delivered, and
　　wherein the selecting circuit selects the type of delivery by modifying a delivery of the video stream to limit the potential risk of worsening the adverse condition based on biometrics.

6. The method of claim 1, embodied in a cloud-computing environment.

7. A computer-implemented video stream control method, comprising:
　　analyzing, via a processor, a video stream to identify, apriori, a section of the video stream where an adverse condition will occur by determining, apriori, that a likelihood of the section of the video will have a negative effect is greater than a first predetermined threshold;
　　delivering, via a computer, a notification that the adverse condition will occur in the section of the video stream and modifying the video stream before the section of the video stream is played; and
　　selecting, via the processor, a type of delivery of the section of the video stream that includes a modified version of the section omitting the adverse condition based on a set of rules factoring the adverse condition and user data at a time of the notification,
　　wherein the selecting, after the notification is delivered, queries for authorization to watch the unmodified version of the section of the video stream,
　　wherein a timing of the notification varies based on a user input, and
　　wherein a sensitivity of the analyzing the video stream identifying the adverse condition varies based on a user constraint to a predetermined threshold of biometric data required to trigger the adverse condition,
　　further comprising learning a plurality of user reactions to the video stream to optimize the identification of the adverse condition by the analyzing the video stream.

8. The computer-implemented method of claim 7, wherein the user data comprises biometric data such that the set of rules causes the selecting to select a type of delivery based on avoiding a health risk caused by viewing the video stream comprising the adverse condition as determined by the biometric data, and
　　wherein the biometric data includes data determined based on an interval of time.

9. The computer-implemented method of claim 7, wherein the user data comprises a user preference such that the set of rules causes the selecting to select a type of delivery customized preference, and
　　wherein the notification includes a textual description of the section of the video stream.

10. A computer program product for video stream control, the computer program product comprising a non-transitory computer readable storage medium having program instructions embodied therewith, the program instructions executable by a computer to cause the computer to perform:
　　analyzing a video stream to identify, apriori, a section of the video stream where an adverse condition will occur by determining, apriori, that a likelihood of the section of the video will have a negative effect is greater than a first predetermined threshold;
　　delivering a notification that the adverse condition will occur in the section of the video stream and modifying the video stream before the section of the video stream is played; and
　　selecting a type of delivery of the section of the video stream that includes a modified version of the section omitting the adverse condition based on a set of rules factoring the adverse condition and user data at a time of the notification,
　　wherein the selecting, after the notification is delivered, queries for authorization to watch the unmodified version of the section of the video stream,
　　wherein a timing of the notification varies based on a user input, and
　　wherein a sensitivity of the analyzing the video stream identifying the adverse condition varies based on a user constraint to a predetermined threshold of biometric data required to trigger the adverse condition.

\* \* \* \* \*